United States Patent
Brenner

(10) Patent No.: US 10,376,227 B2
(45) Date of Patent: Aug. 13, 2019

(54) DENTAL X-RAY SENSOR HOLDER

(71) Applicant: DENTSPLY SIRONA Inc., York, PA (US)

(72) Inventor: Tod Brenner, Pequea, PA (US)

(73) Assignee: DENTSPLY SIRONA Inc., York, PA (US)

( * ) Notice: Subject to any disclaimer, the term of this patent is extended or adjusted under 35 U.S.C. 154(b) by 268 days.

(21) Appl. No.: 15/658,888

(22) Filed: Jul. 25, 2017

(65) Prior Publication Data

US 2018/0028132 A1 Feb. 1, 2018

Related U.S. Application Data

(60) Provisional application No. 62/366,661, filed on Jul. 26, 2016.

(51) Int. Cl.
*A61B 6/14* (2006.01)
*G03B 42/04* (2006.01)

(52) U.S. Cl.
CPC ............ *A61B 6/145* (2013.01); *G03B 42/042* (2013.01)

(58) Field of Classification Search
CPC ............................... A61B 6/145; G03B 42/042
See application file for complete search history.

(56) References Cited

U.S. PATENT DOCUMENTS

2005/0026104 A1 * 2/2005 Takahashi .............. A61B 1/247
433/31
2017/0065236 A1 * 3/2017 Yao ......................... A61B 6/587

* cited by examiner

*Primary Examiner* — Hugh Maupin
(74) *Attorney, Agent, or Firm* — Dentsply Sirona Inc.

(57) ABSTRACT

A dental x-ray sensor holder 10 for securing an x-ray sensor 1 to a holder using suction created between the sensor and a backing plate 3 of the sensor holder. The dental x-ray sensor holder generally includes a bite block 2 with a first end and a second end, a backing plate 3 affixed to or formed contiguously with the second end of the bite block, and an opening 17 to a cavity 20 in the holder, wherein said cavity 20 leads an evacuation chamber 14 for creating a vacuum between the holder and an X-ray sensor.

12 Claims, 16 Drawing Sheets

DENTAL X-RAY SENSOR HOLDER

BACKGROUND OF THE INVENTION

Field of the Invention

The invention relates generally to dental x-ray media/sensor holders (such as Film, Phosphor Plate or Digital Sensor) and more specifically it relates to a dental x-ray sensor/media holder for securing an x-ray sensor to a holder using suction created between the sensor and a backing plate of the sensor holder.

Related Art

Dental professionals have used x-ray imaging in their line of work for many years. A traditional dental x-ray acquisition involves exposing an x-ray film to x-ray energy after it has passed through site to be irradiated. The film is developed and an image is obtained. The dental x-ray film must be positioned relative to the target site in a predetermined and secure manner in order to obtain a useful image. Many numbers of x-ray film holders and positioning devices have long been known in the art, including for example, that shown in U.S. Pat. No. 3,473,026 which is hereby incorporated by reference for background purposes.

Many dental professionals have replaced traditional x-ray films with x-ray sensors. An example of such a sensor is shown for example in U.S. Pat. No. 6,652,141 which is hereby incorporated by reference for background disclosure of x-ray sensors. Both X-ray sensors and X-ray films are, as is long known in the art, secured in a predetermined position during the x-ray imaging procedure. In a manner similar to the use of x-ray films, holding and positioning devices have been developed for x-ray sensors. Digital sensors often have attached electrical connection cords such that the digital sensor transfers data to a storage or display device such as a computer.

Phosphor imaging plates are also used in the dental industry. The imaging plate is irradiated and the x-ray shot is stored onto the imaging plate to be read later by a scanning machine or the like and the data is transferred to a storage or display device, such as a computer.

These and other type of devices that receive dental x-rays for dental purposes are herein collectively referred to as dental x-ray imaging media, x-ray sensors, sensors, imagers, image media or the like. Any such devices that are sensitive to such x-rays is within the scope of the invention. It will be appreciated from the above discussion that the different image media holders while all accomplishing similar purposes, all operate in different manners. The image media themselves are different in shape, size and configuration. For example, traditional x-ray films are often manufactured inside an envelope before being used with a patient. Phosphor imaging plates are often very thin, not much thicker than a sheet of paper or two and are placed into a barrier envelope before being used in an x-ray procedure. Digital sensors tend to be fairly thick in respective comparison due to the internal energy sensing components required for such devices. It is envisioned that in the future, other type of dental imaging media will be developed using similar or perhaps completely different technologies. These all have at least some commonality in that they generally must fit within the oral cavity and they must be securely held in a desired location during the x-ray procedure.

One way of securing dental imaging media in a desired location is by using adhesives or one or more straps as shown in U.S. Pat. No. 8,573,844 which is hereby incorporated by reference for background purposes. This allows dental professionals to affix the media to a holder which in turn is connected to an aiming ring through a positioning arm, allowing for the aiming ring to be in alignment with the imaging media and the holder. Straps are not aesthetically pleasing and moreover provide extra bulkiness which is not needed while some adhesives are not suitable for use in the oral cavity. Moreover, smaller holders can be produced when these securing means are eliminated. It is therefore desired to create a holder that is small, eliminates the use of adhesives or straps on imaging media and can be used for different sizes, shapes and configuration of imaging media. Given the large number of different imaging media of different sizes, shapes and configurations, and given that many different x-ray procedures may be required in the oral cavity, a dental practitioner will normally keep a large number of imaging media holders in order to be reasonably certain that a proper holder is available at any given time for an x-ray procedure. It takes time and effort to match holders to specific imaging media and it is desired to eliminate this drawback. A need exists therefore for a universal dental x-ray imaging media holder that will securely affix different shapes, sizes and configurations of such imaging media. The present invention provides a holder that meets these desires by securing the x-ray imaging media to the holder using suction created in an evacuation chamber that exists between the sensor and the holder.

BRIEF SUMMARY OF THE INVENTION

The invention generally relates to a dental x-ray sensor holder which includes a bite block with a first end and a second end, a backing plate affixed to or formed contiguously with the second end of the bite block, and an opening to a cavity in the holder, wherein said cavity leads to an evacuation chamber for creating a vacuum between the holder and an X-ray sensor.

There has thus been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a Dental X-ray Sensor Holder for securing an x-ray sensor to a holder using suction created between the sensor and a backing plate of the sensor holder.

Another object is to provide a Dental X-ray Sensor Holder that eliminates the use of releasable or pressure sensitive adhesives and/or one or more straps to affix an X-ray sensor to a backing plate of a sensor holder.

Another object is to provide a Dental X-ray Sensor Holder that has ridges that allow an even evacuation of air between the sensor in a sensor sheath and the backing plate of a sensor holder to create an even suction or vacuum effect to hold the sensor to the holder.

Another object is to provide a Dental X-ray Sensor Holder that is provided with a swivel connection to a suction line to allow for unhindered movement of the suction line or holder when in the oral cavity of a patient.

Another object is to provide a Dental X-ray Sensor Holder with a suction tubing and an adapter for connection to a saliva ejector of a suction system in a dental chair.

Another object is to provide a Dental X-ray Sensor Holder with a suction tubing and an adapter for direct connection to a suction line in a dental chair or vacuum pump without the use of intermediate connections such as a saliva ejector or aspirator hose.

Another object is to provide a Dental X-ray Sensor Holder that can hold any size of sensor by suction.

Another object is to provide a Dental X-ray Sensor Holder with an aiming arm and a suction tubing such that that the suction tubing is embedded inside the aiming/positioning arm to make the holder more compact.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
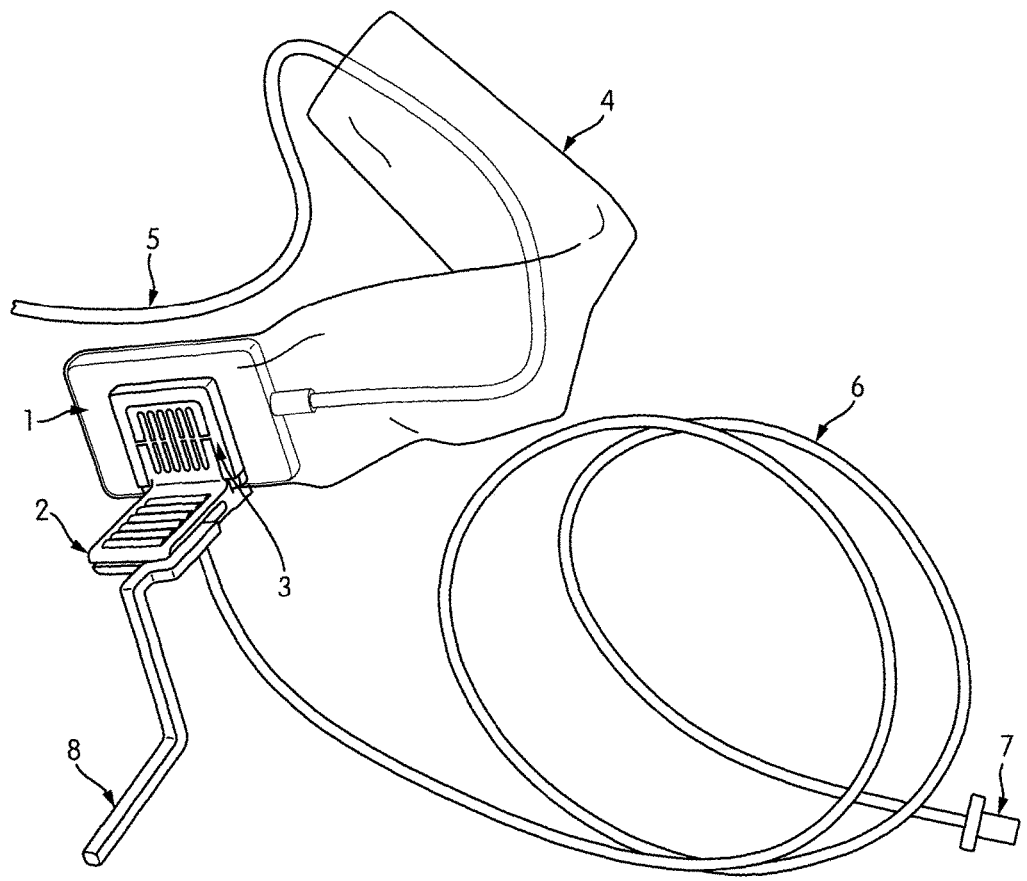
FIG. 1 is a perspective view of a holder in use with an X-ray sensor.

Turning now descriptively to the drawings, in which similar reference characters denote similar elements throughout the several views, the figures illustrate a sensor holder having a bite block with a first end and a second end, a backing plate affixed to or formed contiguously with the second end of the bite block, and an opening to a cavity in the holder, wherein said cavity leads to an evacuation chamber for creating a vacuum between the holder and an X-ray sensor. The cavity, opening and evacuation chamber may be of different configurations, shapes and sizes.

Figure 2:
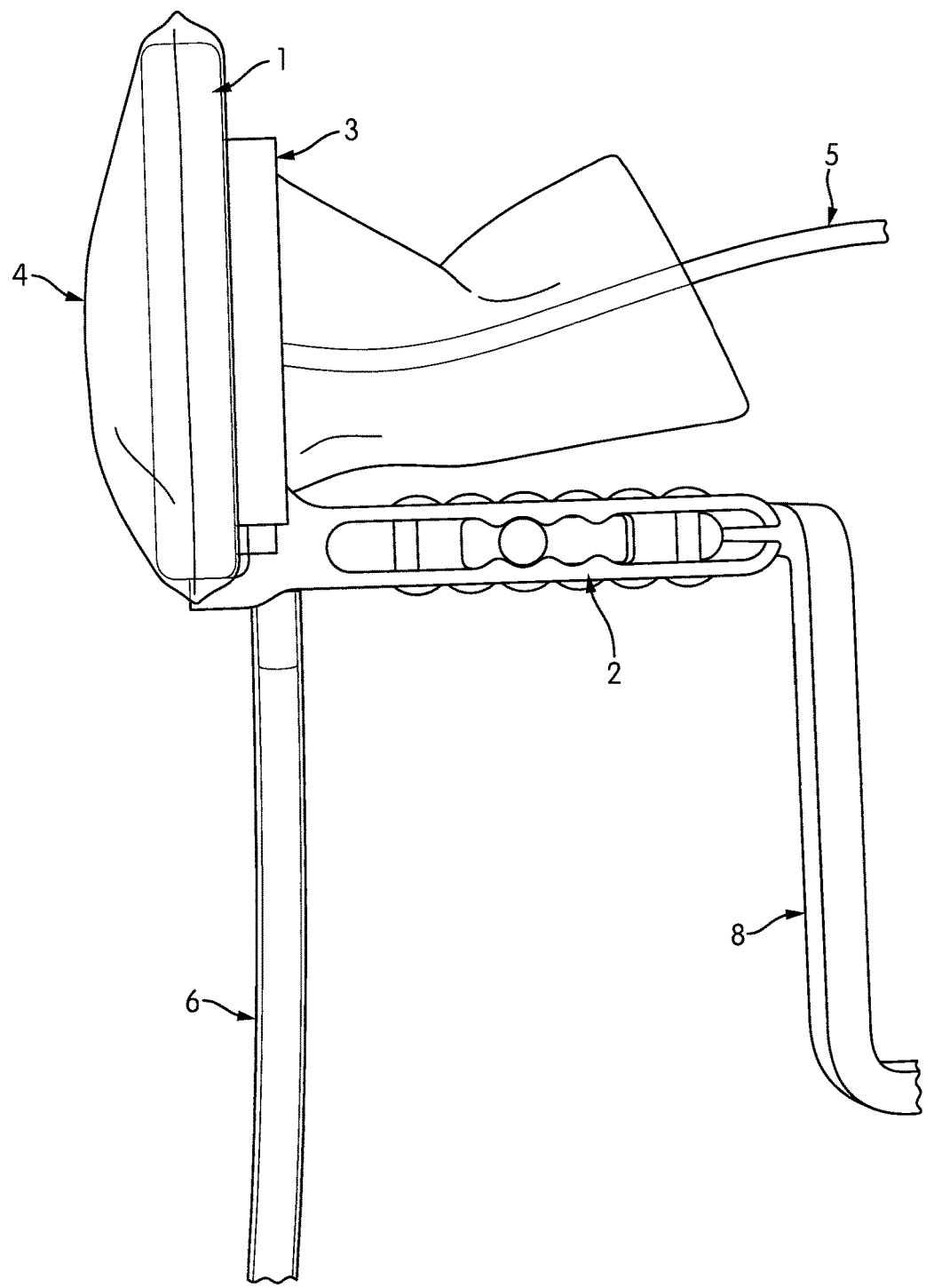
FIG. 2 illustrates a side view of an X-ray sensor securely attached to a sensor holder.
Figure 15:
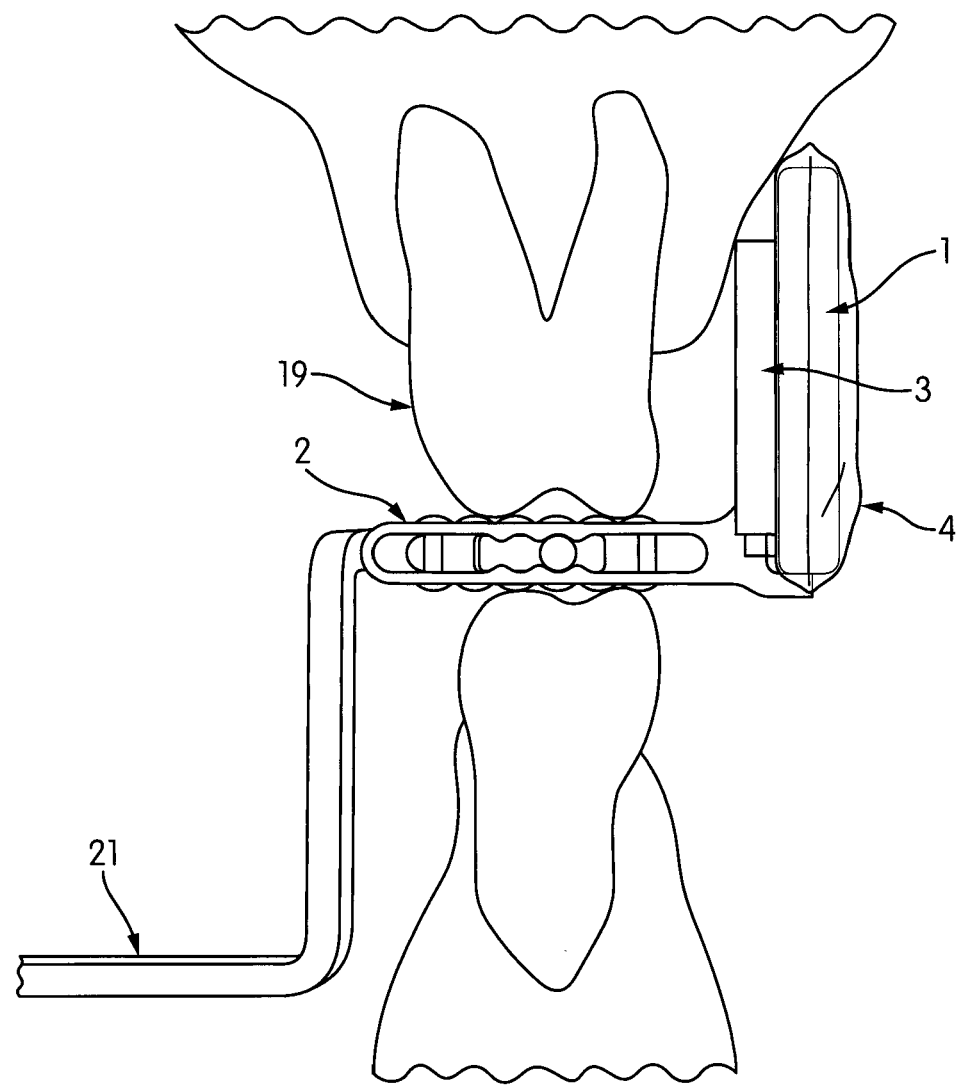
FIG. 15 is a side view of the present invention showing a suction tubing of the holder embedded inside the aiming/suction arm to make the holder more compact.
Figure 16:
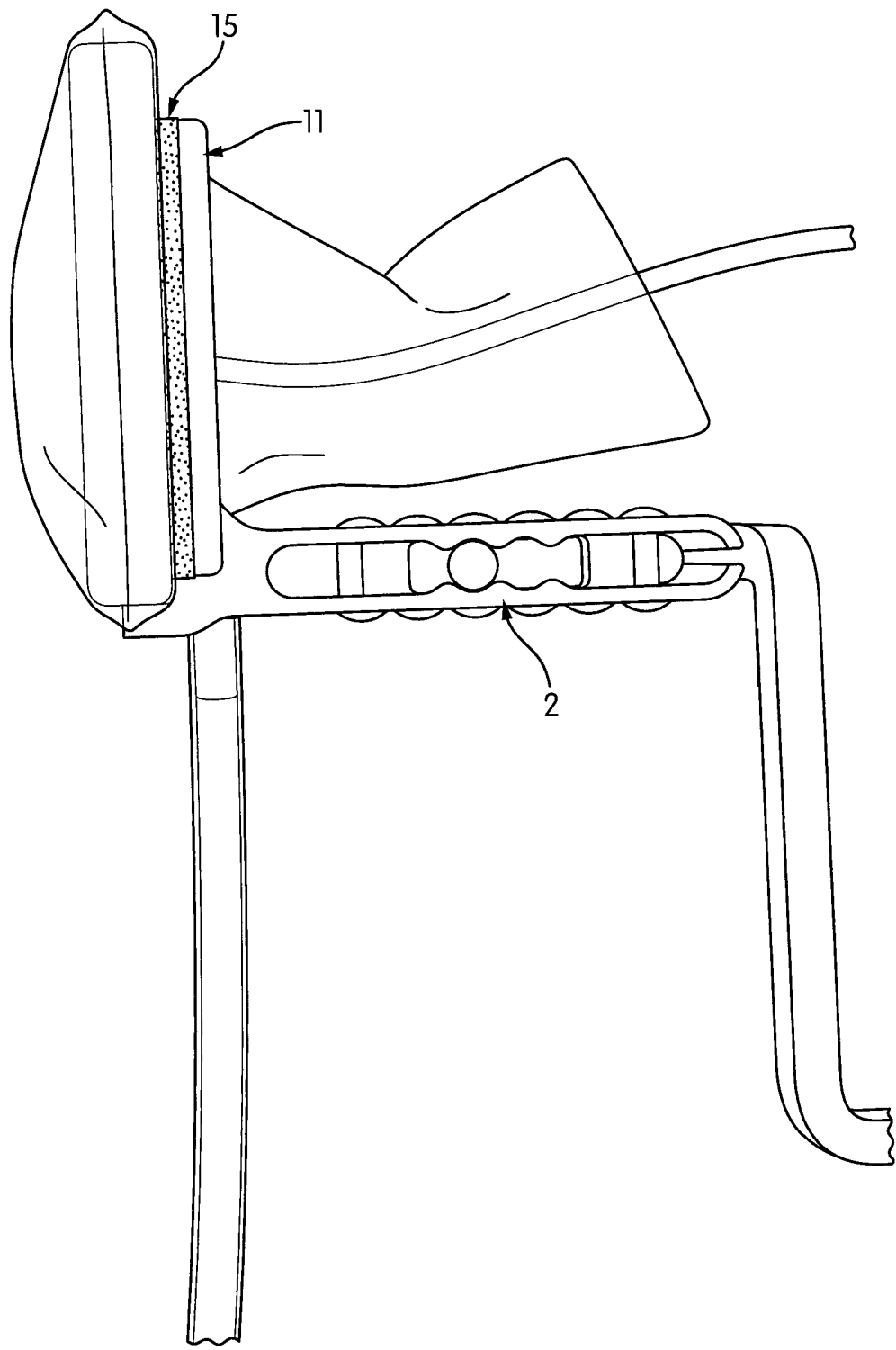
FIG. 16 shows a side view of the second embodiment with a foam attached or bonded to the substrate of the holder.

FIG. 1 and FIG. 2 show a sensor securely attached to an X-ray holder. Referring to FIG. 1, an X-ray sensor 1 is secured to the backing plate 3 of a sensor holder, the sensor being enclosed in a protective sheath 4. A suction tubing 6 is connected to the sensor holder. This allows for the creation of a vacuum between the backing plate of the sensor holder and the sensor/sheath combination when brought together with the suction effect holding the sensor to the backing plate. A positioning/aiming arm 8 is connected to the bite block of the sensor holder preferably through slots or apertures in the bite block and preferable in a friction fit manner. The backing plate is preferably affixed to or formed contiguously with the bite block. An adapter 7 allows for direct or indirect connection to suction lines present on most dental chairs (not shown) or other suction device to create a vacuum that pulls the sensor in tightly and holds it in place until the suction device is turned off. The cable 5 of the X-ray sensor allows for transmission of the sensor data to a receiver in a conventional manner. As is known in the art, the bite block of the X-ray sensor holder will be positioned in a patient's oral cavity (not shown) and the patient will be instructed to bite upon the block. This locates the affixed or supported x-ray image media during the ensuing dental imaging acquisition procedure. Bite block 2 of the invention is of any suitable and conventional design, shape or configuration but can also have the unique inventive aspect of being designed to receive an aiming/suction arm 21 which has a suction tubing embedded in it to make the holder more compact, as shown in FIG. 15.

Figure 3:
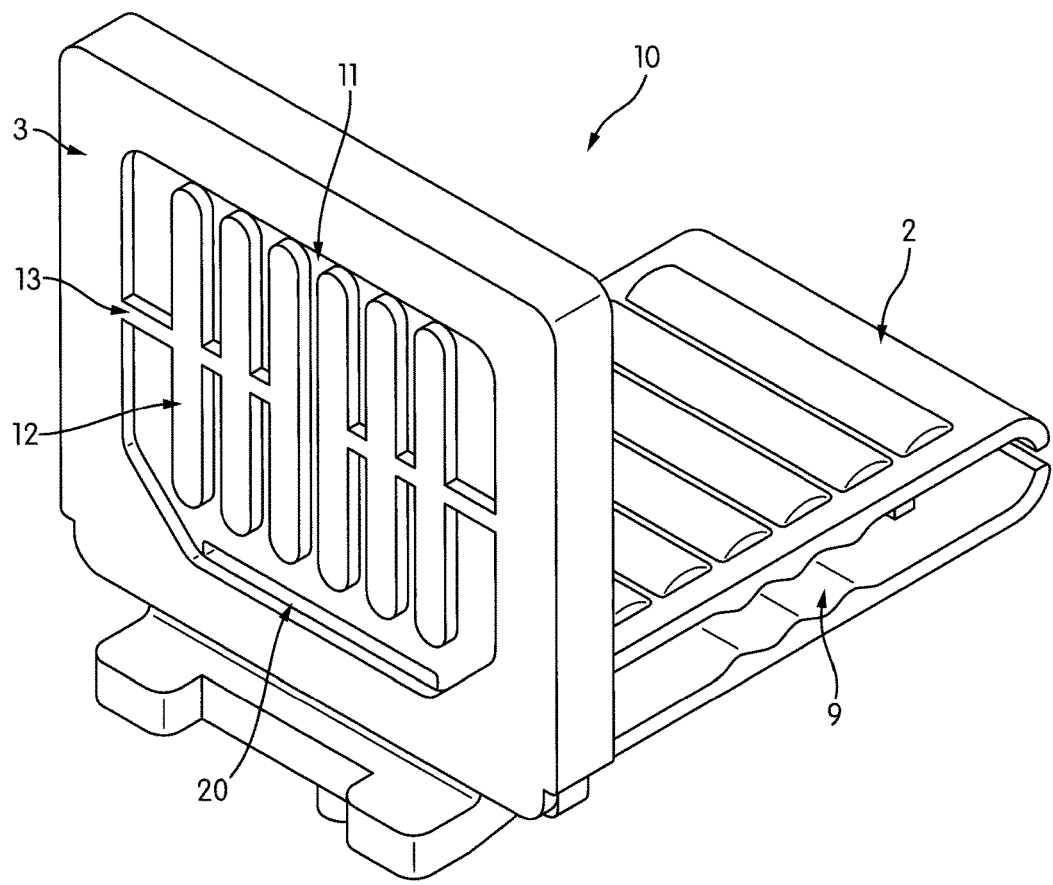
FIG. 3 is a perspective view of the preferred embodiment of the sensor holder. Vertical ridges on the backing plate of the sensor holder allow for even removal of air from the space between the sensor and the plate to create a strong pulling force on the sensor.

Referring to FIG. 3, vertical ridges 12 on the backing plate 3 of the sensor holder allow for an even removal of air from an evacuation chamber 14 (shown in FIG. 7) between the sensor and the plate 3 to create a strong pulling force on the sensor. Air is evacuated from the space between the sensor and the backing plate 3 through the cavity 20. The sensor holder 10 has apertures or slits 9 within which a conventional aiming arm fits. In a preferred embodiment shown in FIG. 3, an elastomeric material is injection overmolded onto the substrate 11 of the backing plate 3 to create a soft outer surface for contact with the sensor to enhance the suction effect. The substrate 11 of the backing plate 3 needs to be a fairly stiff material to assure that the X-ray sensor/media (Film, Phosphor Plate or Digital Sensor) is in parallel alignment with the aiming ring (not shown). Different designs can be realized for the ridges of the backing plate. In all cases, the ridges 12, 13 should be such that an even suction effect is created in the entirety of the evacuation chamber between the X-ray sensor and the backing plate. The ridges could be a part of the substrate 11 or could be a part of the elastomeric surface as in the case of injection overmolding.

Figure 4:
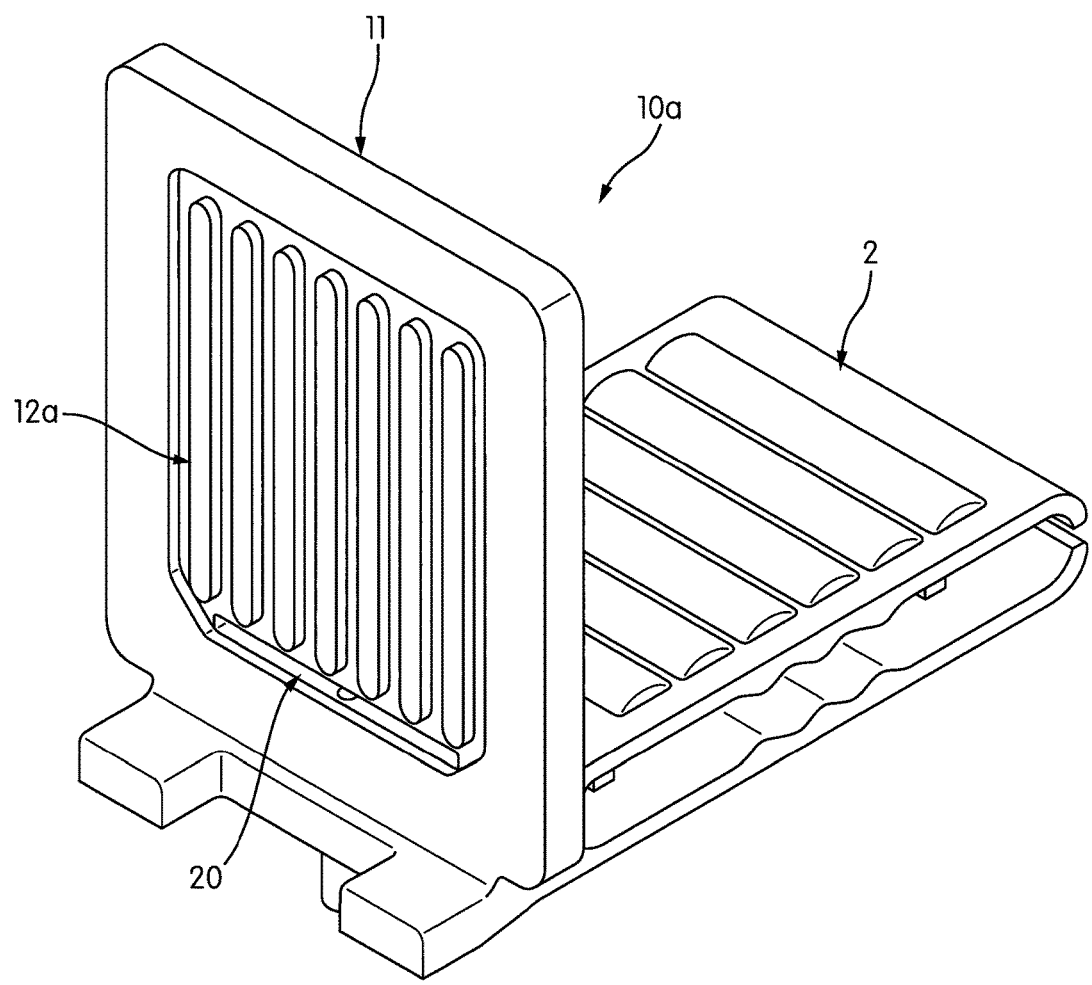
FIG. 4 is a perspective view of the present invention illustrating a second embodiment of the sensor holder. In this embodiment the backing plate is shown as a substrate with no elastomeric material attached or bonded to it.
Figure 6:
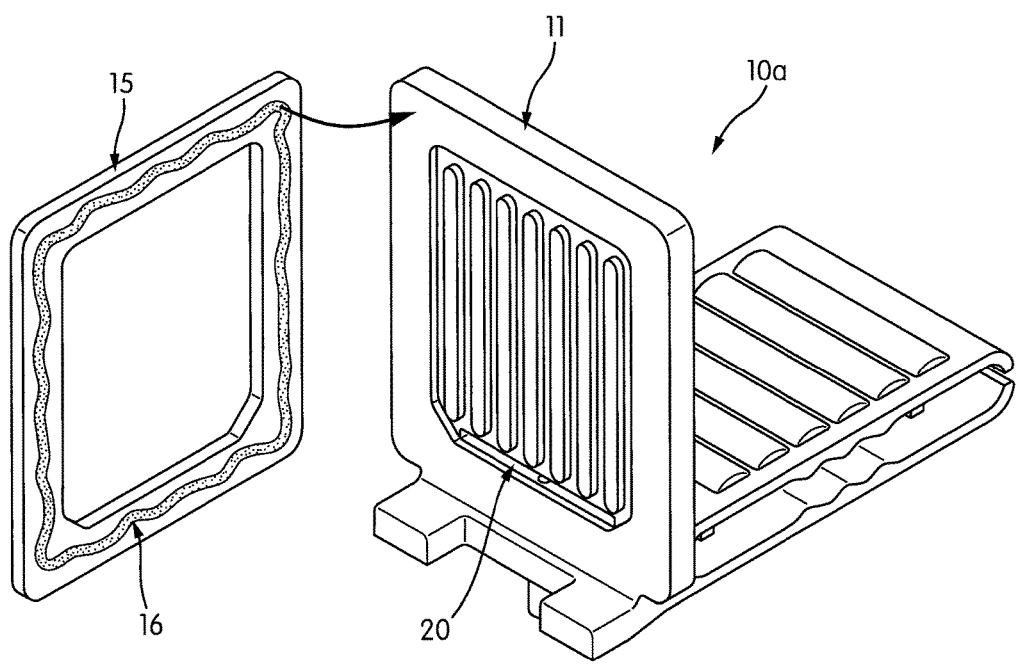
FIG. 6 is a perspective view of FIG. 4 showing the sensor holder with an appropriately shaped foam or foam tape to be attached or bonded to the substrate.

FIG. 4 illustrates a different embodiment of the sensor holder 10a. The backing plate is shown as a substrate 11 with no elastomeric material attached or bonded to it. An appropriately shaped elastomeric material or foam can be bonded or attached to it, as shown in FIG. 6, to enhance the suction effect that secures the sensor in place. Ridges 12a are arranged to provide an evenly distributed suctioning effect.

The soft surface in any embodiment could be, but is not limited to:
1. A permanent, injection overmolded, elastomeric material.
2. An appropriately shaped foam tape that could be permanently adhered to the face of the backing plate.
3. An appropriately shaped self-adhesive foam tape that would be single use and would be removable after use.
4. A removable molded elastomeric sleeve that fits tightly to the upright sensor plate.

Ideally, the foam is a closed cell foam. Closed cell foams generally contain gas bubbles formed during the foam's expansion and cure. The bubbles are permanently locked in place and this enables it to resist liquids such as water and saliva and also act as an insulator and air barrier, enhancing the suction effect in the evacuation chamber.

Figure 5:
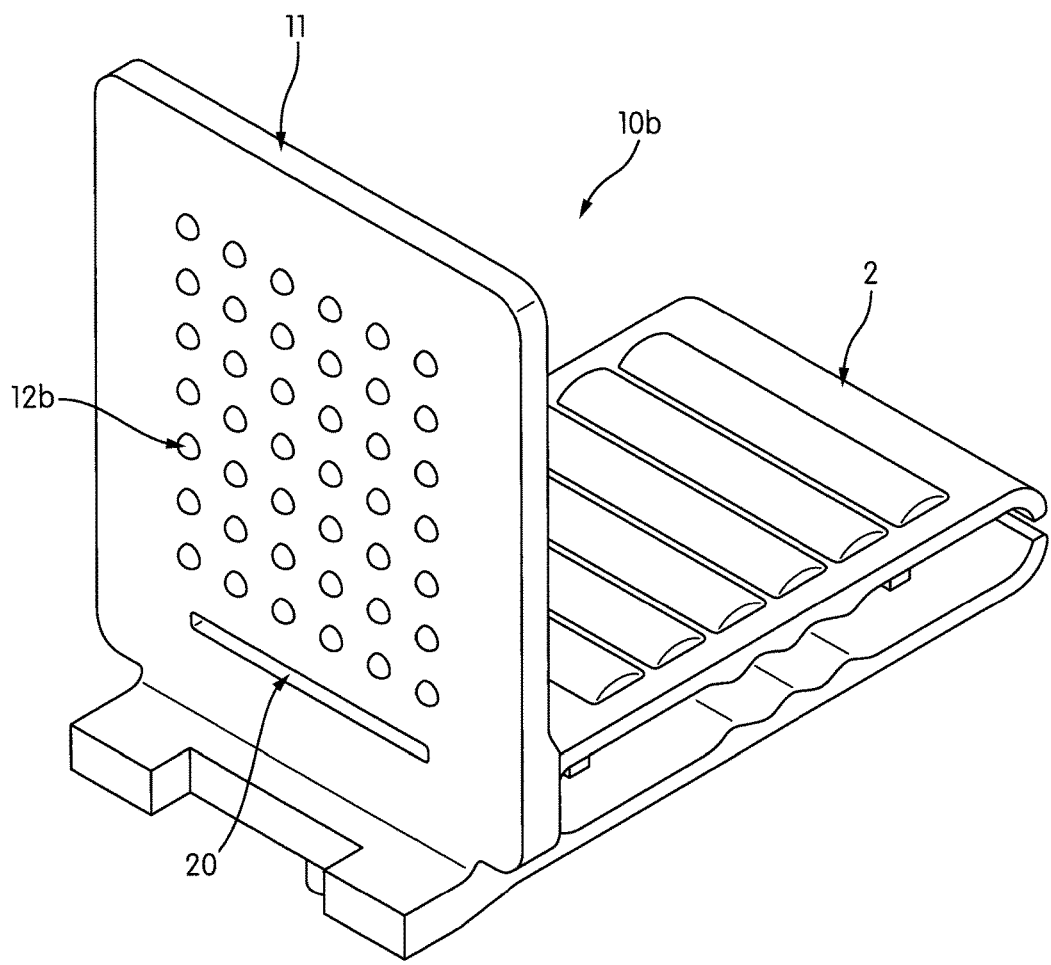
FIG. 5 illustrates a perspective view of a third embodiment of the sensor holder wherein semi spherical protrusions are arranged on the substrate to provide an even suctioning effect.

As shown in FIG. 5, spherical protrusions 12b can be arranged on the substrate 11 to provide an even suction effect.

Figure 7:
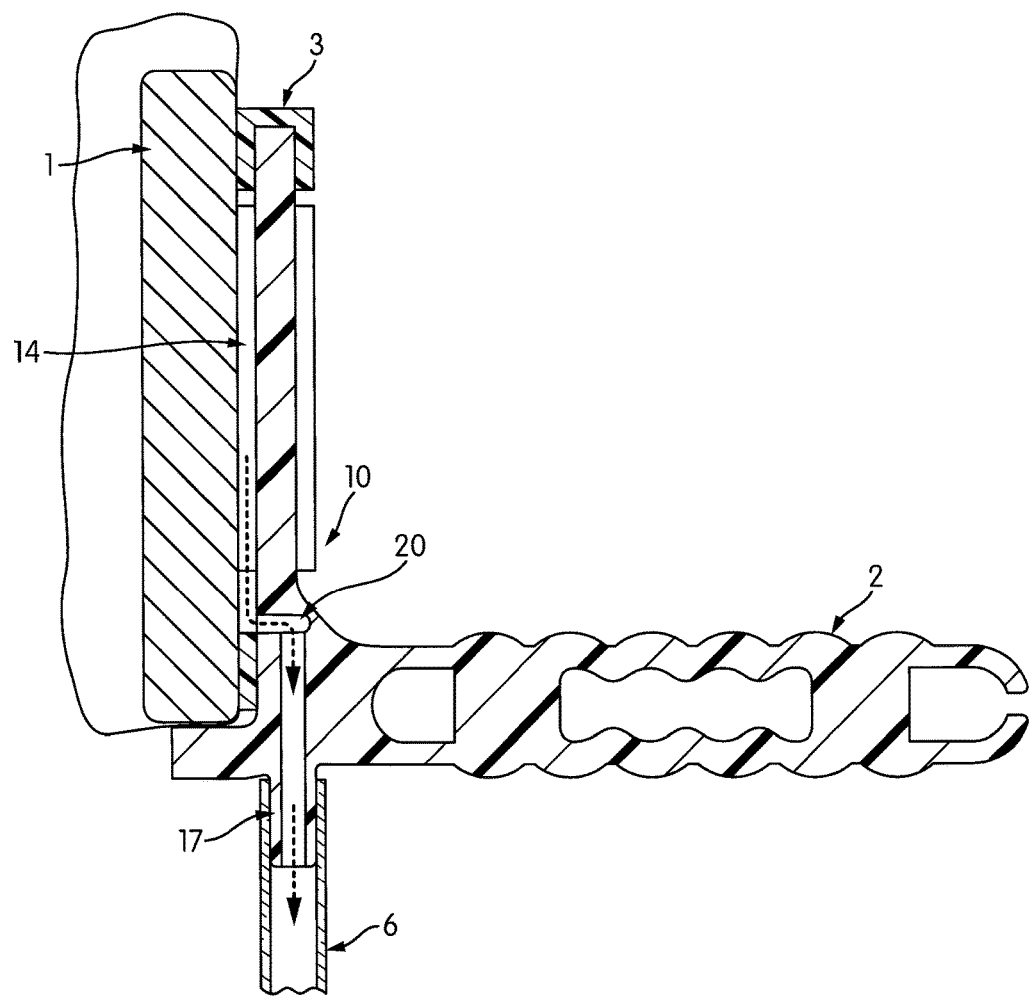
FIG. 7 is a cross sectional view in accordance with the preferred embodiment of the present invention as used with an X-ray sensor showing an opening leading a cavity and then to an evacuation chamber between the holder and the sensor.

FIG. 7 is a cross sectional view of a preferred embodiment of the sensor holder 10 in operation with a suction tubing 6 to secure an X-ray sensor to the backing plate 3 of the holder 10. Air is drawn out of the evacuation chamber 14 in the sensor holder combination to create the vacuum required to hold the combination together. The suction tubing is connected to holder 10 through an extended opening 17, which leads through a cavity 20 to the evacuation chamber 14. The cavity 20 and/or evacuation chamber 14 may be of different configurations, shapes and sizes.

Figure 8:
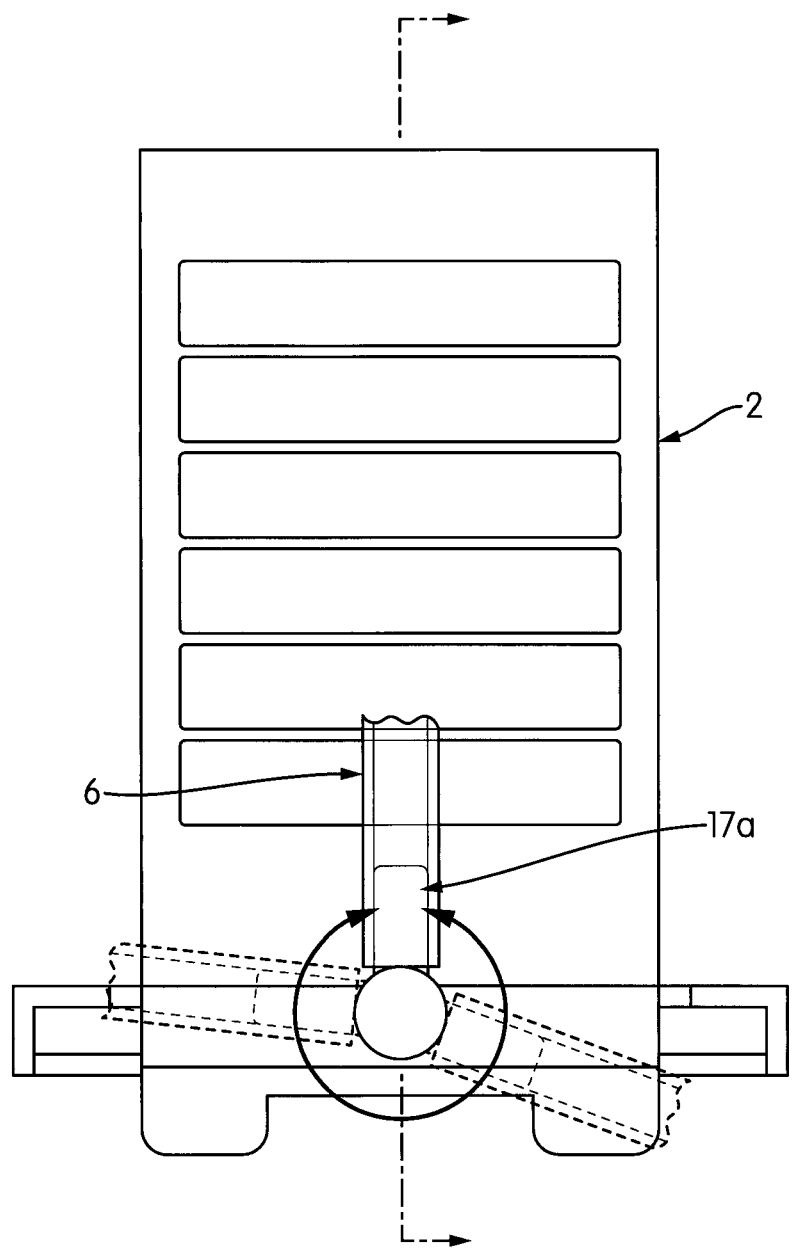
FIG. 8 is a bottom view of the present invention illustrating an extended swivel opening which leads a cavity and then to an evacuation chamber.
Figure 9:
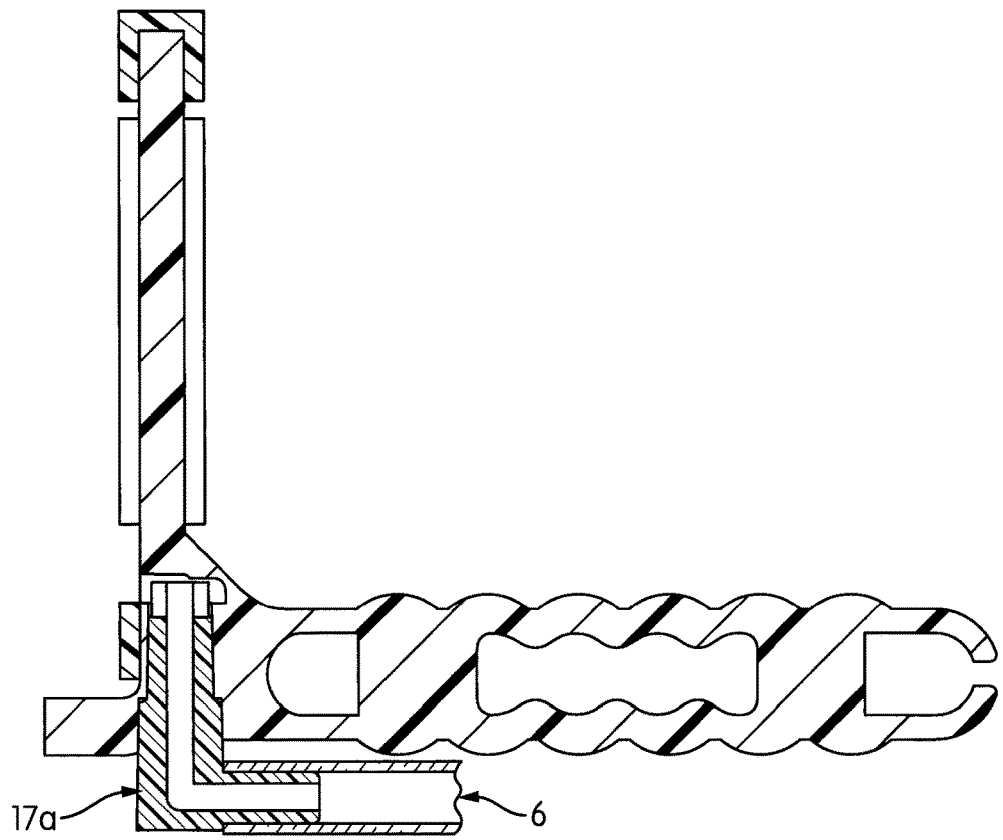
FIG. 9 illustrates a cross sectional view of the preferred embodiment of the sensor with an extended swivel opening for connection to a suction tubing.

The opening 17 can also be of different configurations, shapes and size. In particular, FIG. 8 shows a bottom view of the sensor holder with a swivel opening 17a which extends in the direction of the longitudinal axis of the bite block 2. The swivel opening 17a can additionally be seen in FIG. 9. The opening allows swivel movements of the suction tubing 6 when connected to enable easy placement of the holder in the mouth of a patient. Swivel opening 17a allows suction tubing 6 to be positioned on either side of holder 10 to allow holder 10 to be used in different locations in the oral cavity. Opening 17, tubing 6 and evacuation chamber 14 are in fluid communication.

Figure 10:
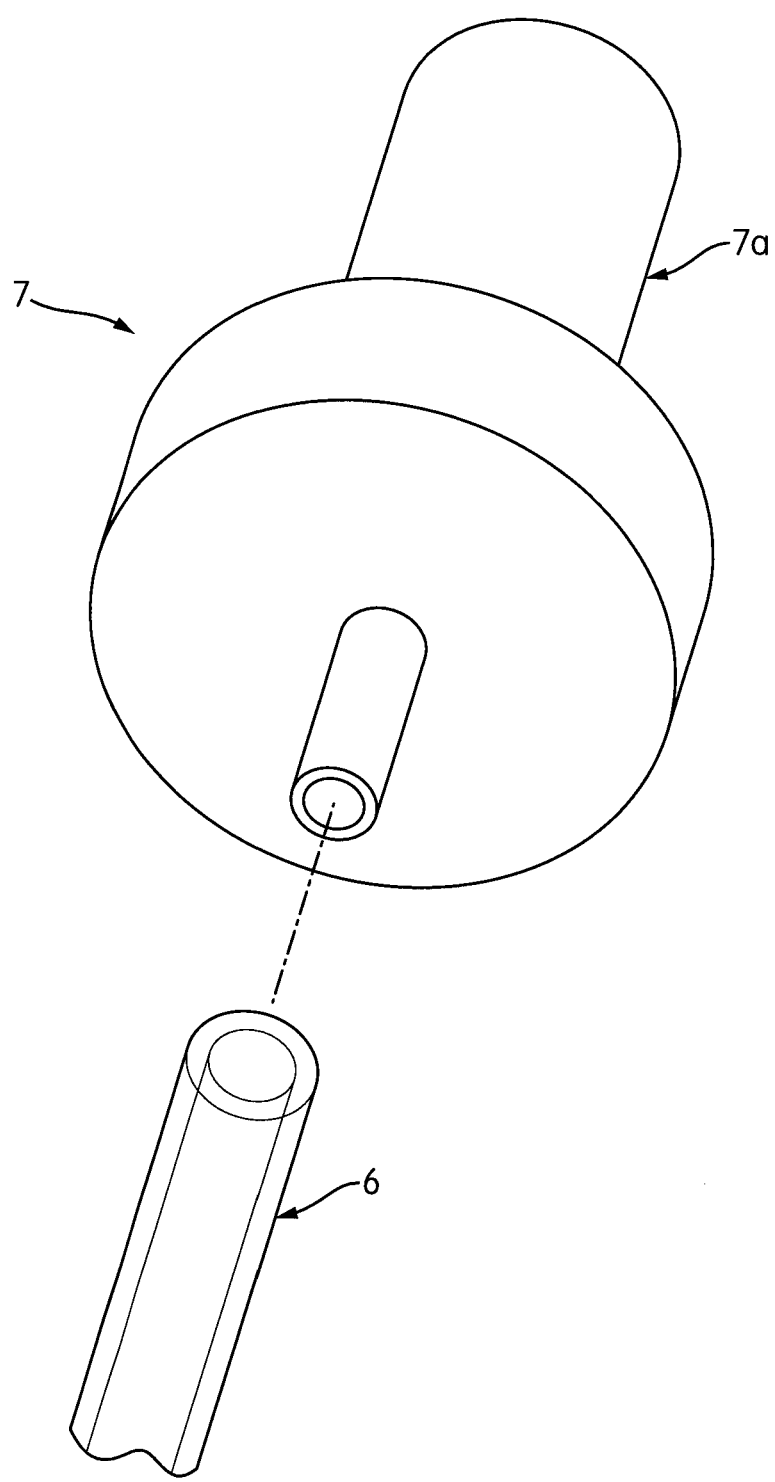
FIG. 10 is a perspective view of an adapter to be connected to a suction tubing.
Figure 11:
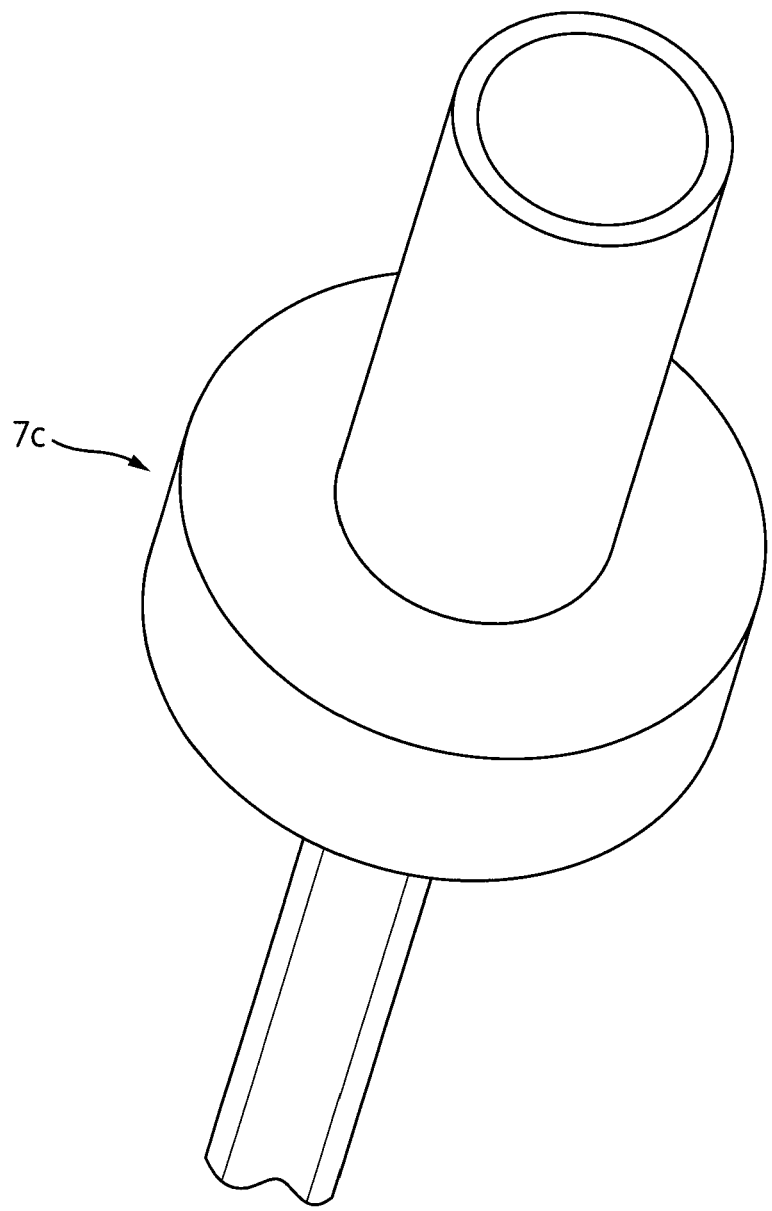
FIG. 11 is a perspective view showing the adapter in connection with the suction tubing.
Figure 12:
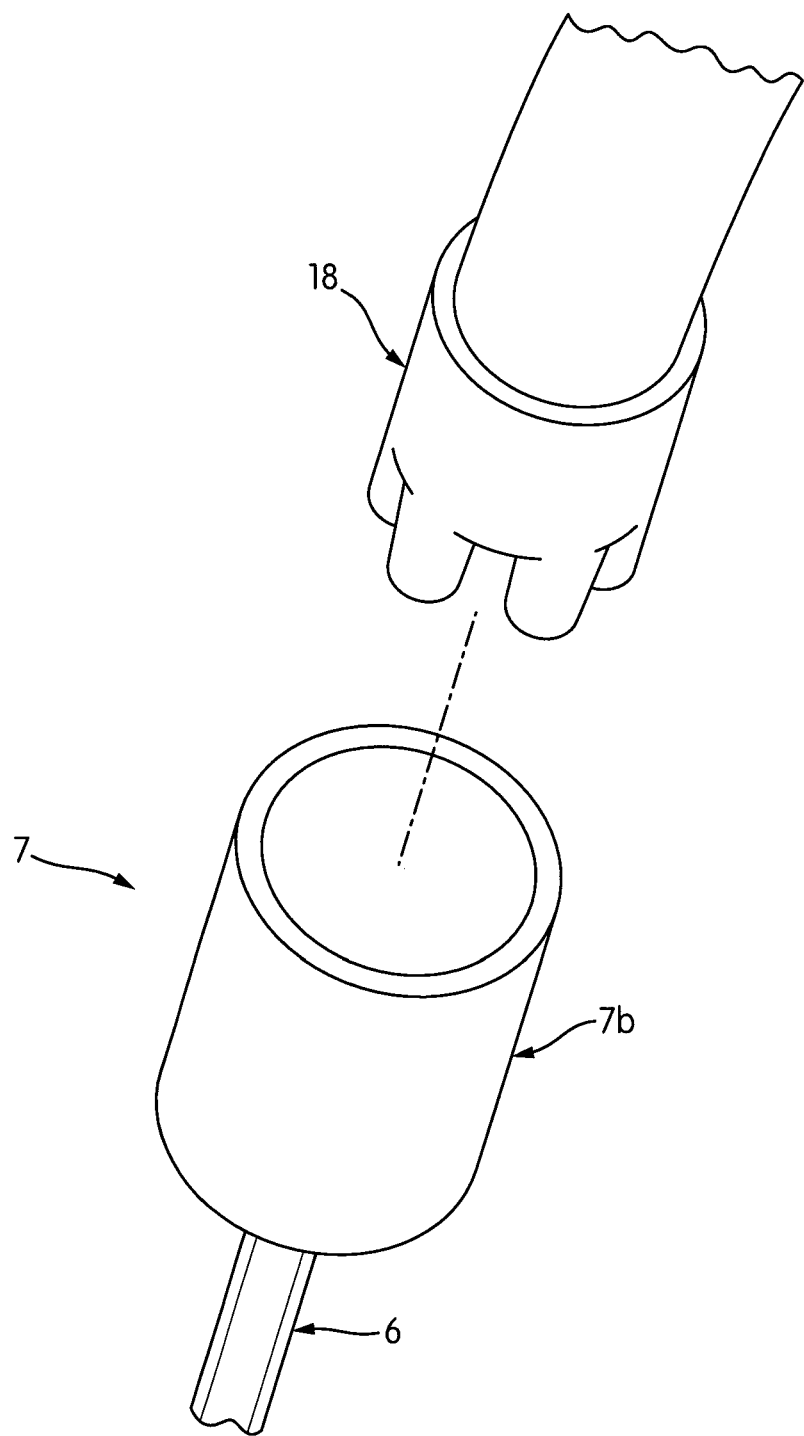
FIG. 12 is a perspective view illustrating another adapter constructed to connect directly to a saliva ejector.
Figure 13:
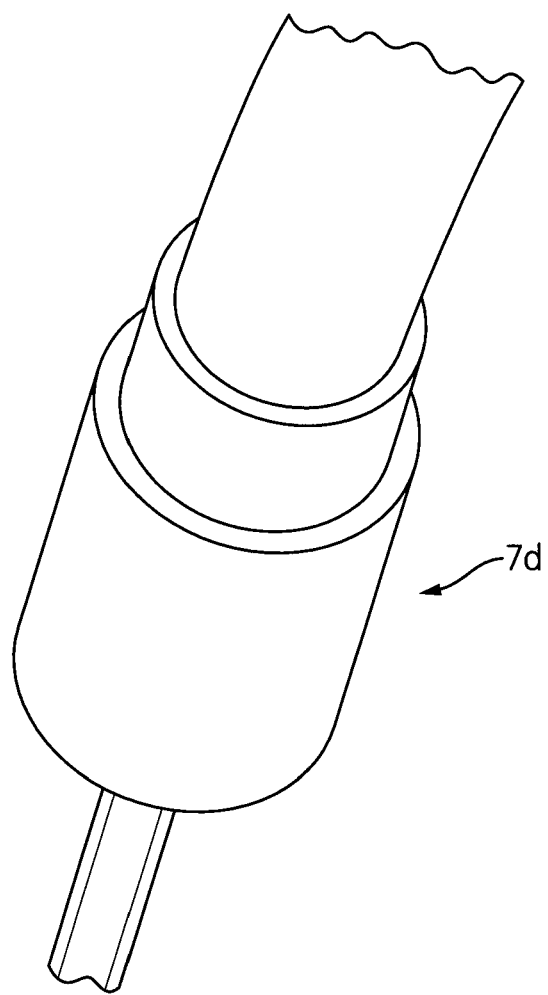
FIG. 13 is a perspective view showing the adapter of FIG. 12 in connection with the saliva ejector of FIG. 12.
Figure 14:
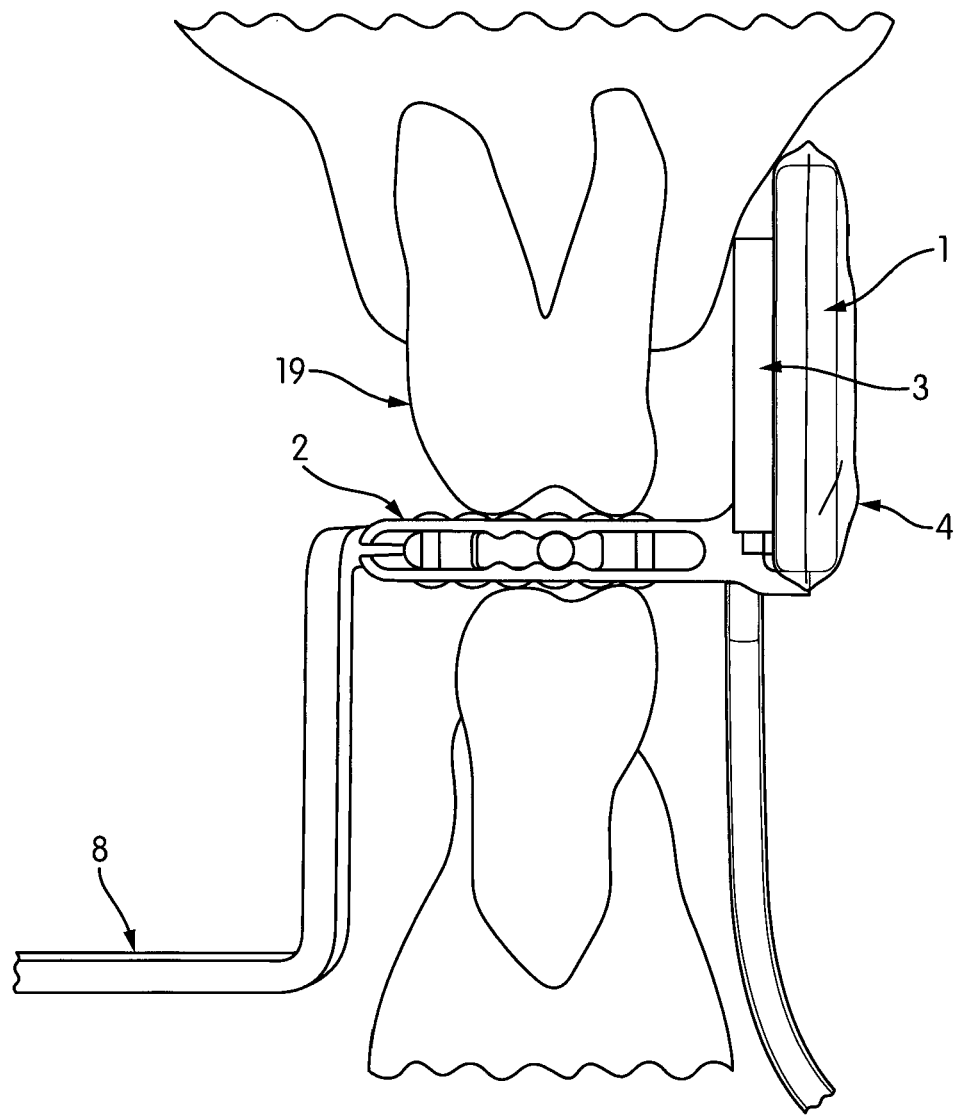
FIG. 14 is a side view illustrating the use of an X-ray sensor, a holder and an aiming/positioning arm in the oral cavity of a patient to take X-ray images.

As shown in FIG. 10, the distal end 7 of the suction tubing 6 can be fitted with an adapter 7 for connection to a suction device such as a saliva ejector or aspirator hand piece (not shown) which in turn in connected to suction units such as the suction unit of a dental chair. Direct connections to suction units such as a vacuum pump can also be realized by using appropriate adapters. 7a shows an adapter to a suction line of a dental chair and 7b shows an adapter to a saliva ejector. In FIG. 12 the adapter 7b is constructed to connect directly and firmly to a saliva ejector 18 to conduct a suction effect through the sensor holder tubing 6 to the evacuation chamber. The adapter 7b receives the saliva ejector preferably through a friction fit manner. The operation of the preferred embodiment of the holder involves holding the bite block 2 in place by teeth 19 and creating a vacuum between the sensor and the backing plate 3 to secure the sensor throughout the image acquisition process as shown in FIG. 14. An aiming/positioning arm 8 connected to an aiming ring (not shown) outside the oral cavity ensures that the sensor and the ring are in alignment. A suction tubing 6, connected on the proximal end to the opening in the holder and on the distal end to an adapter which in turn is connected to a suction device, provides a medium through which air is evacuated from the evacuation chamber 14 when the suction device (not shown) is engaged. Air is drawn out of the evacuation chamber to create a vacuum, which has the resultant effect of pulling the sensor securely to the backing plate. The ridges 12,13 on the backing plate ensure an even suction effect is created in the evacuation chamber.

To make the holder even more compact the suction tubing can be embedded inside the aiming/suction arm 21 for connection to the cavity 20 or evacuation chamber 14. This ensures a space saving holder and reduces the mass of material in the oral cavity of the patient during image acquisition.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

REFERENCE NUMERALS

1 Sensor
2 Bite block
3 Backing plate
4 Sheath
5 Sensor cable
6 Suction tubing
7 Adapter
7a Direct connection to suction line
7b Connection to saliva ejector
7c Adapter connected to suction tube
7d Adapter connected to saliva ejector
8 Positioning/aiming arm
9 Slot/aperture
10 Holder with injection overmould
10a Bare Holder with vertical ridges on substrate
10b Bare Holder with spherical protrusions on substrate
11 Substrate
12 Ridge
12a Vertical ridges
12b Spherical protrusions
13 Horizontal ridge
14 Evacuation chamber
15 Foam/Foam tape
16 Adhesive 17 Opening
17a Swivel opening
18 Saliva ejector
19 Tooth
20 Cavity
21 Aiming/Suction arm

The invention claimed is:

1. A dental X-ray imaging media holder comprising:
a bite block with a first end, a second end and apertures, said apertures configured to receive an aiming arm;
a backing plate, with a first side and a second side, said backing plate affixed to or formed contiguously with the second end of the bite block; and
an opening to a cavity in the holder;
wherein said cavity leads to an evacuation chamber, at the second side of the backing plate, for creating a vacuum between the holder and an X-ray imaging media to secure the X-ray imaging media to the holder.

2. A dental X-ray imaging media holder according to claim 1,
wherein the backing plate has ridges or protrusions that allow for an even evacuation of air from the evacuation chamber, wherein said evacuation chamber lies between the X-ray imaging media and the backing plate.

3. A dental X-ray imaging media holder according to claim 2,
wherein the backing plate comprises a substrate and a soft material, and
wherein the soft material is attached or bonded to said substrate to enhance a suction effect between said X-ray imaging media and said backing plate.

4. A dental X-ray imaging media holder according to claim 3,
wherein the soft material is selected from the group consisting of a permanent injection overmolded elastomeric material, foam tape and removable molded elastomeric sleeve.

5. A dental X-ray imaging media holder according to claim 4,
wherein the foam is a closed cell foam.

6. A dental X-ray imaging media holder according to claim 1,
wherein the opening is constructed to swivel.

7. A dental X-ray imaging media holder according to claim 1, further comprising:
a suction tubing configured to connect the opening to an evacuation line.

8. A dental X-ray imaging media holder according to claim 7,
wherein the evacuation line is a suction line of a dental chair and wherein said suction line is detachably connected to the suction tubing by a first adapter.

9. A dental X-ray imaging media holder according to claim 7,
wherein the evacuation line is a saliva ejector and wherein said saliva ejector is detachably connected to the suction tubing by a second adapter.

10. A dental X-ray imaging media holder according to claim 7,
wherein the said suction tubing is embedded inside the aiming arm.

11. A dental X-ray imaging media holder according to claim 1,
wherein the holder is configured to secure X-ray imaging media of different shapes and sizes appropriate to allow for positioning in a mouth of a patient for acquisition procedures.

12. A method of operating a dental X-ray imaging media holder, comprising:
providing a bite block of the holder to be held between upper and lower teeth of a patient,
fitting an aiming arm into apertures of the bite block,
attaching an X-ray imaging media to a backing plate of the holder, and
creating a vacuum between the backing plate of the holder and the X-ray imaging media to secure the X-ray imaging media to the backing plate.

* * * * *